United States Patent
Irvin

(10) Patent No.: US 9,375,502 B2
(45) Date of Patent: Jun. 28, 2016

(54) AIR FRESHENER WITH SCENTED STRING

(71) Applicant: American Covers, Inc., Draper, UT (US)

(72) Inventor: Aaron Irvin, Salt Lake City, UT (US)

(73) Assignee: American Covers, Inc., Draper, UT (US)

( * ) Notice: Subject to any disclaimer, the term of this patent is extended or adjusted under 35 U.S.C. 154(b) by 443 days.

(21) Appl. No.: 14/066,354

(22) Filed: Oct. 29, 2013

(65) Prior Publication Data

US 2015/0118117 A1    Apr. 30, 2015

(51) Int. Cl.
*A61L 9/12* (2006.01)
*A44C 15/00* (2006.01)
*A44C 25/00* (2006.01)

(52) U.S. Cl.
CPC ............... *A61L 9/127* (2013.01); *A44C 15/002* (2013.01); *A44C 25/007* (2013.01)

(58) Field of Classification Search
CPC .................................. A61L 9/12; A61L 9/127
See application file for complete search history.

(56) References Cited

U.S. PATENT DOCUMENTS

| | | | |
|---|---|---|---|
| 3,994,439 A | 11/1976 | Van Breen et al. | |
| 5,071,889 A | 12/1991 | Boucaud | |
| 5,569,511 A | 10/1996 | Spector | |
| 5,919,423 A | 7/1999 | Requejo et al. | |
| 6,051,547 A | 4/2000 | Ornitz | |
| 6,391,398 B1 | 5/2002 | Pesu et al. | |
| 8,474,637 B2 | 7/2013 | Zhang et al. | |
| 2004/0082263 A1* | 4/2004 | Parrish | A63H 33/22 446/245 |
| 2012/0052037 A1* | 3/2012 | Sivik | C11D 17/041 424/70.11 |

FOREIGN PATENT DOCUMENTS

| | | | |
|---|---|---|---|
| CN | 101067222 A | 11/2007 | |
| CN | 102767015 A | 11/2012 | |
| FR | 2667482 A1 | 4/1992 | |

* cited by examiner

*Primary Examiner* — Sean E Conley

(74) *Attorney, Agent, or Firm* — Thorpe, North & Western LLP

(57) ABSTRACT

An air freshener comprises a flexible strand formed of polymer and having a solid consistency. The strand is elongated and has a length greater than a diameter. The strand is flexible to bend under a weight of the strand. A desired fragrant material, different from the polymer, has a desired fragrance and is interspersed within the polymer of the strand. The strand can be coupled to and carried by the carrier. The carrier can be rigid. A talisman can be coupled to and carried by the carrier.

25 Claims, 3 Drawing Sheets

AIR FRESHENER WITH SCENTED STRING

BACKGROUND

1. Field of the Invention

The present invention relates generally to air fresheners.

2. Related Art

Air fresheners can be used to provide an aesthetically pleasing scent in a desired area. Some air fresheners are configured for a particular space or use. An air freshener configured for one space or use, may not be well suited for another space or use.

SUMMARY OF THE INVENTION

It has been recognized that it would be advantageous to develop an air freshener to provide a desired scent. In addition, it has been recognized that it would be advantageous to develop an air freshener with an effective surface area for dispensing the desired scent. Furthermore, it has been recognized that it would be advantageous to develop an air freshener that is flexible and capable of being adapted to various different forms and conditions.

The invention provides an air freshener comprising a flexible strand formed of polymer and having a solid consistency. The strand is elongated and has a length greater than a diameter. The strand is flexible to bend under a weight of the strand. A desired fragrant material, different from the polymer, has a desired fragrance and is interspersed within the polymer of the strand.

In accordance with a more detailed aspect of the invention, the air freshener can comprise a carrier with the strand coupled to and carried by the carrier. The carrier can be rigid. The air freshener can further comprise a talisman coupled to and carried by the carrier.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The term "scent material" and "fragrant material" are used interchangeably herein to refer broadly to a material that carries a desired fragrance or scent that can be discernible or smelled, or even a neutralizing agent. Thus, the scent or fragrance can be an ascertainable smell used to cover other scents, or a neutral agent that eliminates odors or provides a fresher atmosphere. In addition, the scent or fragrance can be determined by human olfactory sense and transmitted through the air.

The term "talisman" is used broadly herein to refer to a decorative element, such as an amulet, charm, trinket, or the like. The talisman can also provide a useful structure to the air freshener.

Description

Figure 1:
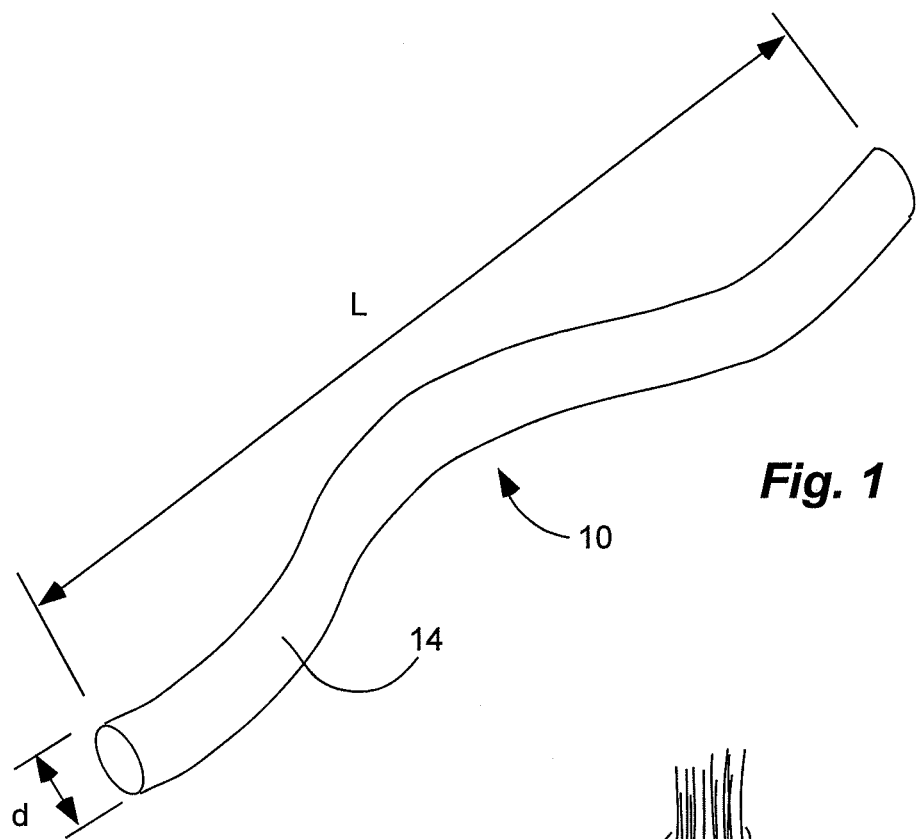
FIG. 1 is a perspective view of an air freshener in accordance with an embodiment of the present invention.

As illustrated in FIG. 1, an air freshener, indicated generally at 10, in an example implementation in accordance with the invention is show. The air freshener can include a flexible polymer strand with a fragrant material interspersed therein and having a fragrance or scent that permeates out of the polymer of the strand over time. The fragrant material can have a desired fragrance or scent, different than a scent of the polymer. The air freshener can provide an aesthetically pleasing scent or fragrance, as well an aesthetically pleasing appearance, in a space, such a vehicle, locker, closet, room, etc. The air freshener or the strand can be formed into a loop, and can be provided with a carrier and/or a talisman.

The air freshener can include a stand 14 that can be flexible and elongated. The strand can be flexible enough that it bends and flexes under a force of gravity, and can be incapable of holding or maintaining its own shape or configuration, and can bend under its own weight. Thus, the strand 14 can be easily configured as desired, and can conform to other shapes or objects, such as a carrier. Thus, the strand can be incorporated into various different air fresheners and/or configurations. In addition, the strand 14 can be elongated, and can have a length L much greater than a width or diameter d. In one aspect, the strand can have a diameter d between $\frac{1}{16}$ and $\frac{1}{4}$ inch, and a length L greater than 8 inches. Thus, the strand can be provided in sufficient length and flexibility to be used with other objects or items. In addition, the strand 14 can have a solid consistency and a solid and consistent material throughout a cross-section or thickness and length thereof. In one aspect, the strand can have a circular cross-sectional shape to facilitate wrapping or braiding the strand. In another aspect, the strand can have other cross-sectional shapes, such as oblong, oval, square, triangular, star, starburst, etc., to increase surface area for scent release. Furthermore, the strand can be formed of polymer or a polymer material. In one aspect, the strand can comprise polyvinyl chloride (PVC). The strand can be formed by extrusion.

A desired fragrant material is interspersed within the polymer or polymer material of the strand 14. The polymer material and the fragrant material can form a consistent mixture throughout the cross-section or thickness and length of the strand. The fragrant material can have a desired fragrance or scent that diffuses out of the polymer material of the strand over time. The desired fragrance or scent can be different from any scent of the polymer, or the naturally occurring scent of the polymer. The fragrant material can be a scented oil or the like, and can be mixed with the polymer material prior to forming the strand, with the mixture being extruded together as a single, consistent, monolithic body.

The strand 14 can be utilized as an air freshener 10 itself, or by itself. Alternatively, as described above, the strand can be incorporated into different shapes, forms, configurations or air fresheners.

Figure 2:
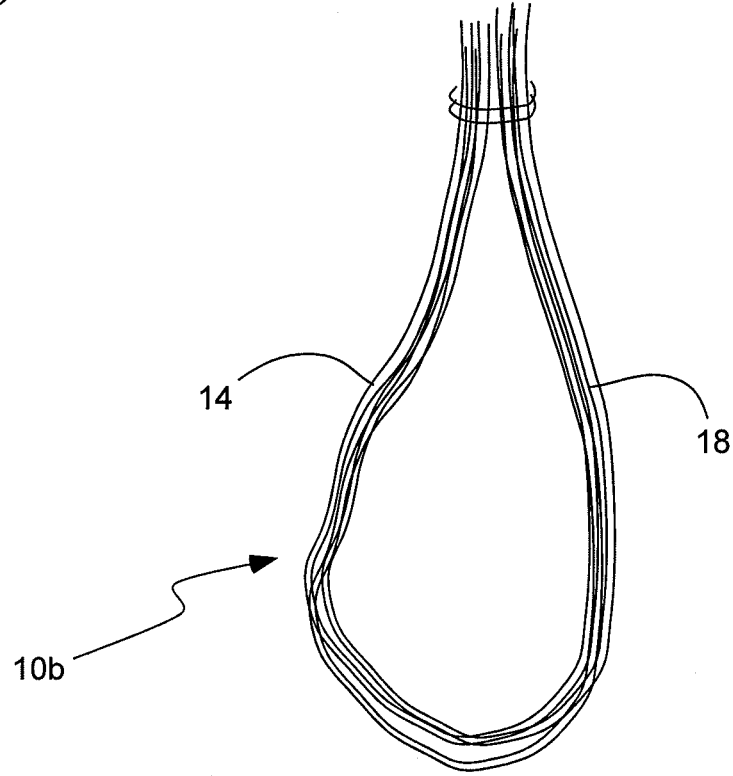
FIG. 2 is a front view of another air freshener in accordance with another embodiment of the present invention.

The strand 14 can form a loop 18 to form another air freshener 10b, as shown in FIG. 2. The strand can include opposite ends that can be brought together and joined, such as in a knot, to form the loop. The loop can have a diameter of at least 5 inches, when laid out in a circular configuration, so that the loop can be hung, such as from a rear view mirror. The strand 14, and thus the loop 18, can be flexible, and bendable under its own weight due to gravity, to form an elongated loop. In addition, a plurality of strands can be joined together in a parallel configuration to form a multi-strand loop, as shown in FIG. 2. The multiple strands can provide increased surface area that can result in greater scent release.

The air freshener can include a carrier to carry or support and hold the strand or strands. The carrier can provide form and structure, such as shape and configuration, to the strand. In addition, the carrier can wholly or partially surround the strand to resist contact between the strand and other objects, which can resist leaching of the fragrant material from the polymer and onto the other objects. In one aspect, the carrier can be rigid and self supporting. In another aspect, the carrier can be flexible like the strand, but can also have greater strength than the strand. Thus, the carrier can be stronger than the strand. In one aspect, the carrier can be formed of a natural material, or a natural occurring material, such as twin, cotton, wood, bamboo, etc. In another aspect, the carrier can be formed of synthetic, or non-naturally occurring, materials, such as plastic, polymer, etc. In one aspect, the carrier can be formed of a material that can be porous or fibrous. Such materials can contact the strand, and can absorb any fragrant material that leaches from the polymer. In addition, the porous or fibrous material can have increased surface area that can increase the surface area to help with the evaporation of such leached fragrant material.

Figure 3:
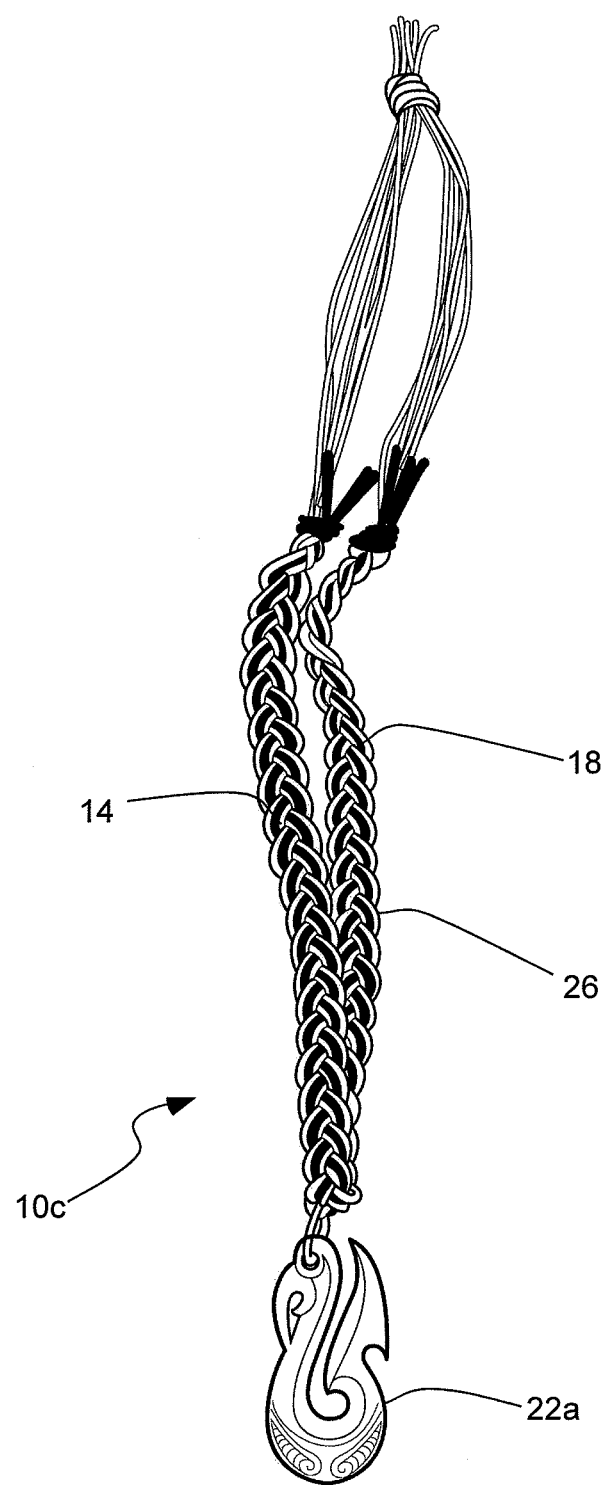
FIG. 3 is a front view of another air freshener in accordance with another embodiment of the present invention.
Figure 4:
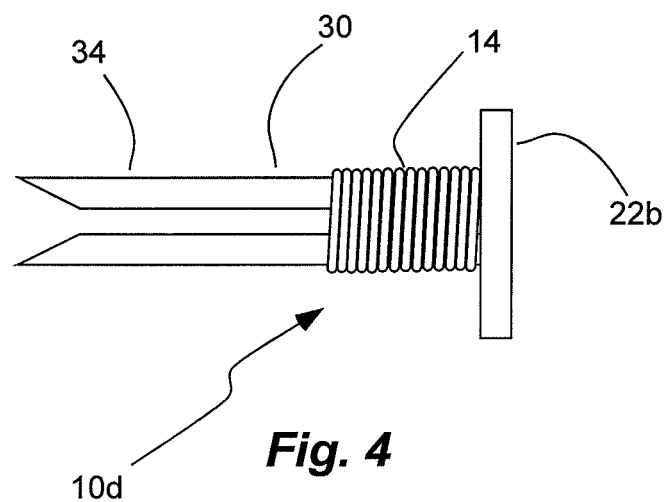
FIG. 4 is a side view of another air freshener in accordance with another embodiment of the present invention.

In addition, the air freshener can include a talisman 22a or 22b that can be coupled to and carried by the carrier, and/or the strand, as shown in FIGS. 3 and 4. The talisman can be flexibly or rigidly affixed with respect to the carrier. The talisman can include a decorative or ornamental item. In addition, the talisman can be formed of a natural or synthetic material. The talisman can be utilized to grasp the air freshener without grasping the strand or touching the fragrant material. The talisman, the carrier, or both, can obscure at least a portion of the strand. Thus, the talisman and/or the carrier can resist grasping and touching of the strand and fragrant material. The carrier can have a length greater than a length of the strand, and with the strand extending only partially along the length of the carrier. Again, the carrier can resist the strand, and thus the fragrant material from coming into contact with other surfaces.

Referring to FIG. 3, an air freshener 10c can have a carrier comprising a plurality of strings 26. The strings 26 and the strand(s) 14 can be intertwined together, such as braided together. The strings can partially surround the strands to resist contact between the fragrant material of the strands and other surfaces. In addition, the strings can provide greater strength than the strands. The strings 26 can also be flexible like the strands, and the strings and strands can together form a loop 18 that can be hung from a rear view mirror. The talisman 22a can be suspended from the loop. Again, the strings can provide a stronger loop than the strands alone. The strings and the strands together can be flexible to provide a flexible loop. As described above, the ends of the strings and/or the strands can be brought together and joined to form the loop, such as by wrapping in a knot. Also, as described above, the strings 26 can be longer than the strands 14. Thus, the strings can resist the strands from contacting other surfaces, such as the rear view mirror. The strings 26 can be formed of a material different than the material of the strand 14. For example, the plurality of strings can be formed of a natural material and a fibrous material such as twine or cotton string. The plurality of fibers can have spaces there between. Thus, the fibers of the strings can provide greater surface area to help absorb fragrant material and assist in evaporation of fragrant material.

Referring to FIG. 4, an air freshener 10d can have a carrier comprising a vent clip 30 with a pair of rods 34 or arms extending parallel with respect to one another, and with a gap there between, configured to engage a louver of an air vent. The talisman 22b can be coupled to the vent clip 30 with the pair of rods 34 extending from a back of the talisman. Thus, the talisman can form a head of the vent clip. The strand(s) 14 can be wrapped around the vent clip 30, such as in a coil. The vent clip can be longer than the strand or coil to resist contact of the fragrant material with other surfaces. The talisman 22b or head of the vent clip can be larger than the coil and can provide a grip to resist grasping the strands or coil, and touching the fragrant material. The vent clip 30 can be substantially rigid and can impart rigidity to the strand so that the strand is rigid on the vent clip. The vent clip 30 can be formed of a natural material, such as wood or bamboo. Such natural material can provide pores to absorb the fragrant material and resist contact with other surfaces.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device, comprising:
   a) a flexible strand formed of polymer and having a solid consistency, and being elongated and having a length greater than a diameter, the strand being flexible to bend under a weight of the strand;
   b) a desired fragrant material different from the polymer and having a desired fragrance and interspersed within the polymer of the strand;
   c) a carrier with the strand coupled to and carried by the carrier; and
   d) the carrier further comprises:
      i) a plurality of strings formed of a material different than the strand; and
      ii) the plurality of strings and the strand being intertwined together.

2. The air freshener device in accordance with claim 1, wherein the strand forms a loop.

3. The air freshener device in accordance with claim 1, wherein the strand comprises polyvinyl chloride (PVC).

4. The air freshener device in accordance with claim 1, wherein the strand further comprises a plurality of strands arranged in parallel.

5. The air freshener device in accordance with claim 1, wherein the carrier comprises a natural material.

6. The air freshener device in accordance with claim 1, wherein the carrier further comprises:
   a talisman coupled to and carried by the carrier.

7. The air freshener device in accordance with claim 6, wherein the carrier, or the talisman, or both, obscure at least a portion of the strand.

8. The air freshener device in accordance with claim 1, wherein the carrier has a length and the strand extends only partially along the length of the carrier.

9. The air freshener device in accordance with claim 1, wherein the plurality of strings are formed of a natural material.

10. The air freshener device in accordance with claim 1, wherein the plurality of strings are formed of a fibrous material with a plurality of fibers with spaces between.

11. The air freshener device in accordance with claim 1, wherein the plurality of strings and the strand are braided together.

12. The air freshener device in accordance with claim 1, wherein the plurality of strings and the strand form a loop; and wherein the talisman is suspended from the loop.

13. The air freshener device in accordance with claim 1, wherein the plurality of strings and the strand are wrapped in a knot.

14. The air freshener device in accordance with claim 1, wherein the plurality of strings and the strand together are flexible.

15. The air freshener device in accordance with claim 1, wherein the strand has a diameter between 1/16 and 1/4 inch, and a length greater than 8 inches.

16. An air freshener device, comprising:
   a) a flexible strand formed of polymer and having a solid consistency, and being elongated and having a length greater than a diameter, the strand being flexible to bend under a weight of the strand;
   b) a desired fragrant material different from the polymer and having a desired fragrance and interspersed within the polymer of the strand; and
   c) a carrier with the strand coupled to and carried by the carrier; and
   d) the carrier further comprises:
      i) a vent clip with a pair of rods extending parallel with respect to one another and with a gap therebetween configured to engage a louver of an air vent; and
      ii) the strand being wrapped around the vent clip.

17. The air freshener device in accordance with claim 16, wherein the vent clip is formed of a natural material.

18. The air freshener device in accordance with claim 16, wherein the strand forms a coil around the vent clip.

19. The air freshener device in accordance with claim 16, further comprising a talisman coupled to the vent clip with the pair of rods extending from a back of the talisman.

20. The air freshener device in accordance with claim 16, wherein the vent clip is rigid and imparts rigidity to the strand so that the strand is rigid on the vent clip.

21. The air freshener device in accordance with claim 19, wherein the carrier, or the talisman, or both, obscure at least a portion of the strand.

22. The air freshener device in accordance with claim 16, wherein the carrier has a length and the strand extends only partially along the length of the carrier.

23. An air freshener device, comprising:
   a) a flexible strand formed of polymer and having a solid consistency, and being elongated and having a length greater than a diameter, the strand being flexible to bend under a weight of the strand;
   b) the strand comprising polyvinyl chloride (PVC);
   c) a desired fragrant material different from the polymer and having a desired fragrance and interspersed within the polymer of the strand;
   d) the strand forming a loop;
   e) the strand having a diameter between 1/16 and 1/4 inch, and a length greater than 8 inches;
   f) a carrier with the strand coupled to and carried by the carrier, the carrier being rigid;
   g) the carrier comprising a natural material;
   h) the carrier having a length and the strand extends only partially along the length of the carrier; and
   i) a talisman coupled to and carried by the carrier.

24. The air freshener device in accordance with claim 23, wherein the carrier further comprises:
   a) a plurality of strings;
   b) the plurality of strings and the strand being braided together;
   c) the plurality of strings being formed of a natural material and a fibrous material with a plurality of fibers with spaces between;
   d) the plurality of strings and the strand forming the loop with the talisman suspended from the loop; and
   e) the plurality of strings and the strand are wrapped in a knot.

25. The air freshener device in accordance with claim 23, wherein the carrier further comprises:
   a) a vent clip with a pair of rods extending parallel with respect to one another and with a gap therebetween configured to engage a louver of an air vent;
   b) the vent clip being formed of a natural material;
   c) the strand being wrapped around the vent clip;
   d) the strand forming a coil around the vent clip; and
   e) the talisman being coupled to the vent clip with the pair of rods extending from a back of the talisman.

* * * * *